United States Patent [19]

Erpenbach et al.

[11] 4,252,983

[45] Feb. 24, 1981

[54] PRODUCTION OF ACETIC ANHYDRIDE AND ACETIC ACID FROM ACETALDEHYDE

[75] Inventors: Heinz Erpenbach, Cologne; Klaus Gehrmann, Erftstadt; Alfred Hauser, Erftstadt; Kurt Karrenbauer, Erftstadt; Winfried Lork, Erftstadt, all of Fed. Rep. of Germany

[73] Assignee: Hoechst Aktiengesellschaft, Fed. Rep. of Germany

[21] Appl. No.: 969,102

[22] Filed: Dec. 13, 1978

[30] Foreign Application Priority Data

Dec. 22, 1977 [DE] Fed. Rep. of Germany ....... 2757222

[51] Int. Cl.$^3$ ................... C07C 51/235; C07C 53/08; C07C 53/12
[52] U.S. Cl. ..................................... 562/536; 260/546
[58] Field of Search ......................... 562/536; 260/546

[56] References Cited

U.S. PATENT DOCUMENTS

| | | | |
|---|---|---|---|
| 2,170,002 | 8/1939 | Benson | 562/536 |
| 3,119,862 | 1/1964 | Alheritere | 562/536 |

FOREIGN PATENT DOCUMENTS 273191 5/1969 U.S.S.R. .................................. 562/536

*Primary Examiner*—Vivian Garner
*Attorney, Agent, or Firm*—Connolly and Hutz

[57] ABSTRACT

Acetic acid and acetic anhydride are produced continuously from acetaldehyde which is reacted by oxidizing it with gaseous oxygen in liquid phase in the presence of copper acylate and cobalt acylate as a catalyst and in the presence of an aliphatic carboxylic acid ester as a diluent. More specifically, the reaction is effected at temperatures of 62° to 90° C. over a period of less than 20 minutes with the use of the diluent and acetaldehyde in a quantitative ratio of 60:40 to 40:60; the resulting reaction products are delivered to a distilling zone in which the carboxylic acid ester and water are distilled off overhead and separated into two phases. Next, the organic phase is recycled with a reflux ratio of at least 1:1 to the distilling zone; base product accumulating in the distilling zone is delivered to an evaporating zone in which 2 to 12 parts by weight of an acetic acid/acetic anhydride-mixture as distillate are produced per part by weight of catalyst solution as base product.

3 Claims, 1 Drawing Figure

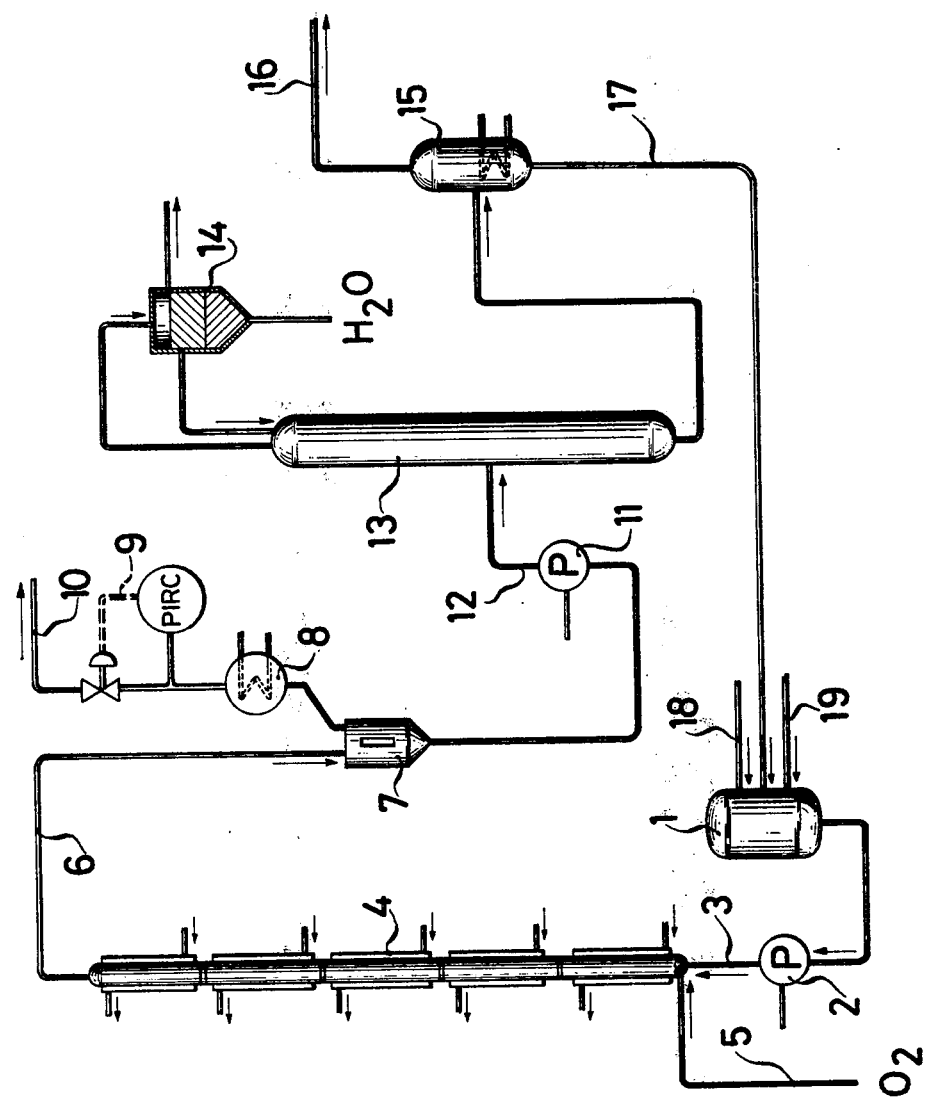

PRODUCTION OF ACETIC ANHYDRIDE AND ACETIC ACID FROM ACETALDEHYDE

This invention relates to a process for making acetic anhydride and acetic acid from acetaldehyde.

The production of acetic anhydride, as the principal product, and acetic acid, as a by-product, by subjecting acetaldehyde to oxidation in contact with copper acylate and cobalt acylate as a catalyst, in liquid or gas phase has already been described (cf. Stanford Research Institute, Menlo Park, California, U.S.A., Report No. 37 A (March 1973), pages 171-179; Ullmann's Encyklpädie der technischen Chemie, 4th edition, volume 11 (1976), pages 81-82; and German Patent Specification No. 1 192 637).

Pure oxygen in admixture with ethyl acetate and acetic acid is used for oxidizing acetaldehyde in liquid phase, at 40° to 60° C. The resulting liquid reaction products are removed from the reactor jointly with the diluent and catalyst. Next, the diluent, catalyst and unreacted acetaldehyde are recycled to the reactor. In order to obtain optimum yields of 70 mol % of acetic anhydride in the liquid phase processes described heretofore, it is necessary to ensure the conversion of not more than 70 to 80% of the acetaldehyde used and to employ a feed mixture containing ethyl acetate and acetaldehyde in a ratio by weight of 70:30.

In the gas phase processes described heretofore, acetaldehyde and air are admitted to the reactor at 60° C., the reactor containing a mixture of acetic anhydride, acetic acid, high boiling constituents and catalyst, and 4 to 6 weight % of acetaldehyde. The resulting gaseous reaction products are removed from the reactor jointly with unreacted acetaldehyde and air in excess. Next, acetaldehyde and the bulk of air are recycled to the reactor. In this latter process, it is again necessary for the acetaldehyde to be subjected to partial conversion, namely to an extent of 30 to 50%, so as to obtain acetic anhydride in a yield of 70 to 80 mol %.

The liquid phase and gas phase processes described hereinabove are obviously not free from adverse effects. While the liquid phase process compares favorably in its higher acetaldehyde conversion rate with the gas phase process, the fact remains that it is not fully satisfactory inasmuch as more acetic acid is obtained at the expense of a correspondingly reduced yield of acetic anhydride. Apart from the considerably lower acetaldehyde conversion rate, it is necessary in the gas phase process to employ an energy-expensive gas cycle system for the removal of the gaseous reaction products. The economy of the liquid and gas phase processes is, however, most seriously affected by the fact that the acetaldehyde undergoes more or less partial conversion which makes it necessary for relatively large proportions of unreacted acetaldehyde to be recycled and worked up.

The present invention now provides a process for the continuous production of acetic acid and acetic anhydride by reacting acetaldehyde by oxidizing it with gaseous oxygen in liquid phase in the presence of copper acylate and cobalt acylate as a catalyst and in the presence of an aliphatic carboxylic acid ester as a diluent, which comprises: effecting the reaction at temperatures of 62° to 90° C. over a period of less than 20 minutes with the use of the diluent and acetaldehyde in a quantitative ratio of 60:40 to 40:60; delivering the resulting reaction products to a distilling zone; distilling off overhead the carboxylic acid ester and water; separating the carboxylic acid ester phase from the water phase and recycling the organic phase with a reflux ratio of at least 1:1 to the distilling zone; delivering base product accumulating in the distilling zone to an evaporating zone and evaporating it therein so as to obtain 2 to 12 parts by weight of an acetic acid/acetic anhydride-mixture as distillate per part by weight of catalyst solution as base product.

Further preferred features of the present invention provide:

(a) for the reaction to be effected in an elongated reaction zone in upright position and for the calculated quantity of gaseous oxygen to be admitted to the reaction zone through a plurality of openings arranged at different levels, and (b) for the reaction zone to be fed with a quantity of gaseous oxygen necessary to have an oxygen content of less than 5 volume % in the issuing gas.

The present process obviates the adverse effects described hereinabove. The reaction zone preferably is a customary tower reactor into which the required quantity of oxygen is introduced through a plurality of openings distributed along the reaction path. In accordance with the present invention it is possible to convert more than 95% of acetaldehyde to desirable material and obtain acetic anhydride in yields of more than 70 mol %, based on the acetaldehyde which undergoes conversion. In addition to this, use can be made in the present process of feed mixtures which contain considerably more acetaldehyde, i.e. 40 weight %, than the feed mixtures employed in the prior art methods.

It is good practice in accordance with this invention to effect the reaction under a pressure of 1 to 5 bars, preferably 2.5 to 3 bars. It is also good practice to effect the reaction over a period of 6 to 12 minutes at temperatures of 65° to 75° C.

The reaction mixture should preferably contain the copper and cobalt acylates in a ratio by weight, calculated as $CuO:Co_3O_4$, of 1:0.25-1. Acetates are the acylates which are preferably used and which should be employed in an overall concentration of 0.08–0.2 weight %, calculated as $CuO+Co_3O_4$, based on the reaction mixture. The carboxylic acid esters should preferably be selected from ethyl acetate and isopropyl acetate and used in a quantitative ester/acetaldehyde-ratio of 50:50.

It is also advantageous to recycle the organic phase under a reflux ratio of 1.5–2.5:1 to the distilling column and produce, in the evaporator, 6 to 10 parts by weight of an acetic acid/acetic anhydride-mixture as distillate per part by weight of catalyst solution as base product, which is recycled to the reaction zone.

One exemplary form of apparatus for carrying out the process of this invention is shown diagrammatically in the accompanying drawing and described hereinafter with reference thereto.

A mixture composed of acetaldehyde, carboxylic acid ester, acetic acid, acetic anhydride and catalyst coming from a reservoir (1) is delivered by means of a dosing pump (2) and a conduit (3) to the base portion of a reactor (4). At the same time, the quantity of oxygen necessary for oxidation is introduced through a conduit (5) and altogether three openings arranged at different levels into the base portion of the reactor (4). The reactor (4) is subdivided into 5 segments, of which each is provided with a separate cooling jacket. In this manner, it is possible to abstract the quantities of heat which are set free during the strongly exothermal reaction so that approximately the same temperature gradient can be maintained in each segment. The reaction products issue in liquid form near the head of the reactor (4) through a conduit (6). In a separator (7), the liquid is separated from minor proportions of off-gas which is removed from the apparatus through a cooler (8), a pressure-retaining valve (9) and a conduit (10). By means of a dosing pump (11), the liquid products are delivered from the separator (7) via a conduit (12) to a distilling column (13), the level of liquid material in the separator (7) being incidentally maintained constant. The column (13) comprises altogether 40 bubble trays and is provided with a feed material inlet which opens centrally thereinto.

Carboxylic acid ester, unreacted acetaldehyde and reaction water are obtained as distillate near the head of the column (13). The phases are separated in a separator (14) and at least one part of material is refluxed to the column (13), per part of organic phase removed. Product which accumulates in the base portion of the column (13) is delivered to an evaporator (15) from which produced acetic acid and acetic anhydride are removed as distillate through a conduit (16). Base product which contains the catalyst (this latter is dissolved in a mixture composed of acetic acid, acetic anhydride and minor proportions of high boilers) is recycled through a conduit (17), unreacted acetaldehyde is recycled through a conduit (18) and carboxylic acid ester free from water is recycled through a conduit (19) to the reservoir (1).

The following Examples illustrate the invention.

EXAMPLE 1

The feed mixture contained 40 weight % of acetaldehyde, 40 weight % of ethyl acetate, 3.7 weight % of acetic anhydride, 14.1 weight % of acetic acid, 1.93 weight % of high boilers and 0.27 weight % of catalyst (0.18 weight % of Cu-acetate +0.09 weight % of Co-acetate), in a quantitative ratio of the oxides CuO:Co$_3$O$_4$ of 1:0.5 (=0.08 weight % of CuO +0.04 weight % of Co$_3$O$_4$). 4.27 kg/h (4.8 l) of feed mixture, which contained 1708 g (38.8 mols) of acetaldehyde, 160 g of acetic anhydride and 602 g of acetic acid was introduced into the base portion of the reactor (4). The reactor was subdivided into 5 jacketted segments of which each was 0.5 meter long and 24 millimeters wide, and packed. Also introduced into the reactor, together with the feed mixture, was altogether 420 l/h (20 mols) of O$_2$. The oxygen subdivided into three portions in the ratio of 2:1:1 was more particularly introduced into the base portions of the first, second and third segments, respectively. The oxygen was used in a quantity necessary to ensure an O$_2$-content of at most 5 volume % in the gas issuing from the reactor. The temperature inside the individual segments was maintained constant by indirect cooling with water. The temperature inside the reactor was determined by means of thermo-elements placed in a protecting tube. The reaction temperature was 75° C. and the pressure 2.8 bars. Under the operational conditions selected, the reactor had a volume of 800 ml. The contact time accordingly was 10 minutes. 4.9 kg/h of liquid reaction product was taken from the head of the reactor and delivered to the 20th tray in the distilling column (13) provided with altogether 40 trays and 80 mm wide. The head temperature was 70° C., the base temperature 128° C. and the reflux 1.8. 1.92 kg of an ester phase which contained 3 weight % of water and 2.6 weight % (50 g) of acetaldehyde and 0.21 kg of an aqueous phase were obtained under these conditions.

2.77 kg/h of base product was introduced into the evaporator (15) which was operated at 83° C. under a pressure of 173 millibars. The base product was decomposed so as to obtain 6 parts by weight distillate per 1 part by weight catalyst solution as base effluent. This gave (a) 2.37 kg/h of a distillate, which contained 58.2 weight % (1379 g) of acetic anhydride and 41.8 weight % (991 g) of acetic acid and (b) 0.4 kg/h of a catalyst solution, which contained 40 weight % (160 g) of acetic anhydride and 36.8 weight % (147 g) of acetic acid. 96.9% (37.6 mols) of the acetaldehyde used underwent conversion. After deduction of the quantities of acetic acid and acetic anhydride used (not produced) in the feed mixture, the following yields, based on the acetaldehyde which underwent conversion, were obtained: 1379 g/h (13.52 mols)=71.9% of acetic anhydride and 536 g/h (8.93 mols)=23.8% of acetic acid. Acetic anhydride and acetic acid were obtained in a total yield of 95.7%.

The space/time-yields was 1741 g of acetic anhydride+acetic acid per liter of free reactor volume per hour. The catalyst solution and the proportions of "unproduced" acetic acid and acetic anhydride together with minor proportions of unreacted acetaldehyde and ester phase freed from low boilers and water were recycled to the reservoir (1).

EXAMPLE 2

The procedure of Example 1 was repeated but modified as follows:

6.1 kg/h (6.85 l) of feed mixture, which contained 40 weight % (55.5 mols) of acetaldehyde, 15.9 weight % (970 g) of acetic acid, 2.5 weight % (153 g) of acetic anhydride, 40 weight % of ethyl acetate, 1.28 weight % of high boilers and 0.32 weight % of catalyst (Cu-acetate+Co-acetate) in a quantitative ratio of the oxides CuO:Co$_3$O$_4$ of 1:0.5 (=0.093 weight % CuO +0.047 weight % Co$_3$O$_4$) was introduced into the reactor (4). 640 l/h of O$_2$, subdivided into three portions in the ratio of 3:2:1, was introduced into the base portions of the first, second and third segments, respectively. The oxygen concentration maintained in the gas issuing from the reactor was less than 5 volume %. The reaction temperature was 75° C., the pressure 2.8 bars, and the contact time 7 minutes. 6.9 kg/h of reaction product was taken from the head of the reactor. 96% of the acetaldehyde underwent conversion. 2.7 kg/h of an ester phase, which contained 3 weight % of water and 3.6 weight % (97 g) of acetaldehyde, and 0.28 kg/h of an aqueous phase were separated in the distilling column (13) under a reflux of 2. 3.92 kg/h of base product was delivered to the evaporator (15) and decomposed to give 10 parts by weight of distillate per 1 part by weight of catalyst solution as base effluent. This gave 3.56 kg/h of a distillate, which contained 57.9 weight % (2060 g) of acetic anhydride and 42.1 weight % (1500 g) of acetic acid, and 0.36 kg/h of a catalyst solution, which contained 42.5 weight % (153 g) of acetic anhydride and 30.5 weight % (110 g) of acetic acid. After deduction of the quantities of acetic anhydride and acetic acid used in the feed mixture, the following yields, based on the acetaldehyde which underwent conversion, were obtained: 2060 g/h (20.2 mols)=75.8% of acetic anhydride and 640 g/h (10.7 mols)=20% of acetic acid. The total yield was 95.8%. The space/time-yield was 2455 g of acetic anhydride +acetic acid per liter of free reactor volume per hour.

EXAMPLE 3

The conditions were as in Example 1, but isopropyl acetate was substituted as a diluent for ethyl acetate. The reactor (4) was fed, per hour, with 4.27 kg of a feed mixture, which contained 40 weight % (38.8 mols) of acetaldehyde, 40 weight % of isopropyl acetate, 15.6 weight % (666 g) of acetic acid and 2.6 weight % (111 g) of acetic anhydride, and with the quantity of catalyst specified in Example 1. Also introduced into the reactor, together with the feed mixture, was 460 l/h of $O_2$, subdivided into three portions which were admitted at three different places. 4.84 kg/h of reaction product was delivered to the distilling column (13). 1.9 kg/h of an ester phase, which contained 2.8 weight % of water and 2.9 weight % (55 g) of acetaldehyde, and 0.2 kg/h of an aqueous phase were obtained under a reflux of 1.5. This corresponded to an acetaldehyde conversion rate of 96.8%. The quantitative ratio of distillate to base product was 6:1 in the evaporator (15). This gave 2.36 kg/h of distillate, which contained 58.1 weight % (1371 g) of acetic anhydride and 41.9 weight % (989 g) of acetic acid, and 0.38 kg/h of a catalyst solution which contained 29.2 weight % (111 g) of acetic anhydride and 55.2 weight % (210 g) of acetic acid. After deduction of the quantities of acetic anhydride and acetic acid used in the feed mixture, the following yields, based on the acetaldehyde which underwent conversion, were obtained: 1371 g/h (13.44 mols)=71.6% of acetic anhydride and 533 g/h (8.9 mols)=23.7% of acetic acid. The total yield was 95.3% and the space/time-yield was 1731 g of acetic anhydride+acetic acid per liter per hour.

EXAMPLE 4

The conditions were as in Example 1, but the reaction temperature was lowered to 50° C. 4.27 kg/h of a feed mixture which contained 40 weight % (38.8 mols) of acetaldehyde, 15.6 weight % (664 g) of acetic acid and 2.7 weight % (117 g) of acetic anhydride, was used. Altogether 340 l/h of oxygen was used to maintain an oxygen concentration of less than 5 volume % in the gas issuing from the reactor. 4.65 kg/h of reaction product was delivered to the distilling column (13). 2.3 kg/h of an ester phase, which contained 3.6 weight % of water and 22.3 weight % (512 g) of acetaldehyde, and 0.1 kg/h of an aqueous phase were obtained. This corresponded to an acetaldehyde conversion rate of only 70.1%. The quantitative ratio of distillate to base product was 6:1 in the evaporator (15). This gave 1.93 kg/h of a distillate which contained 51.9 weight % (1002 g) of acetic anhydride and 48.1 weight % (928 g) of acetic acid and 0.32 kg/h of a catalyst solution which contained 36.6 weight % (117 g) of acetic anhydride and 41.9 weight % (134 g) of acetic acid. After deduction of the quantities of acetic acid and acetic anhydride used in the feed mixture, the following yields, based on the acetaldehyde which underwent conversion, were obtained: 1002 g/h (9.82 mols)=72.2% of acetic anhydride and 398 g/h (6.63 mols) =24.4% of acetic acid. The total yield was 96.6%. The space/time-yield was 1237 g of acetic anhydride+acetic acid, per liter of free reactor volume per hour.

EXAMPLE 5: (Comparative Example)

The conditions were as in Example 1, but the contact time was increased to 20 minutes. 2.15 kg/h of a feed mixture, which contained 40 weight % (19.5 mols) of acetaldehyde, 17 weight % (365 g) of acetic acid and 1.5 weight % (32 g) of acetic anhydride, was used. Altogether 240 l/h oxygen subdivided into three portions, which were admitted to the reactor (4) at three different places, was used in order to maintain an oxygen concentration of 2 to 5 volume % in the gas issuing from the reactor. 2.435 kg/h of reaction product was delivered to the distilling column (13). 0.92 kg/h of an ester phase, which contained 2.5 weight % of water and 1.85 weight % (17 g) of acetaldehyde, and 0.11 kg/h of an aqueous phase were obtained. This corresponded to an acetaldehyde conversion rate of 98%. This quantitative ratio of distillate to base product was 6:1 in the evaporator (15). This gave 1.205 kg/h of a distillate, which contained 44.2 weight % (533 g) of acetic anhydride and 55.8 weight % (672 g) of acetic acid, and 0.2 kg/h of a catalyst solution, which contained 15.9 weight % (32 g) of acetic anhydride and 68.5 weight % (137 g) of acetic acid. After deduction of the quantities of acetic acid and acetic anhydride used in the feed mixture, the following yields, based on the acetaldehyde which underwent conversion, were obtained: 553 g/h (5.23 mols)=54.7% of acetic anhydride and 444 g/h (7.4 mols)=38.7% of acetic acid. The total yield was 93.4%. The space/time-yield was 888 g of acetic anhydride+acetic acid, per liter of free reactor volume per hour.

In the following Table, Examples 1 to 3 which illustrate the present invention, are compared with comparative Examples 4 and 5. As can be seen, the present process compares favorably with the prior art methods in respect of acetaldehyde conversion rate, acetic anhydride yield and space/time-yield.

TABLE

| Example No. | Temp. °C. | Contact time minutes | Acetaldehyde conversion rate in % | Acetic anhydride yield in % | Space/time-yield in g $Ac_2O$ +AcOH per liter per hour |
|---|---|---|---|---|---|
| 1 | 75 | 10 | 96.9 | 71.9 | 1741 |
| 2 | 75 | 7 | 96.0 | 75.8 | 2455 |
| 3 | 75 | 10 | 96.8 | 71.6 | 1731 |
| 4 | 50 | 10 | 70.1 | 72.2 | 1273 |
| 5 | 75 | 20 | 98 | 54.7 | 888 |

We claim:

1. A process for the continuous production of acetic acid and acetic anhydride by reacting acetaldehyde by oxidizing it with gaseous oxygen in liquid phase in the presence of copper acylate and cobalt acylate as a catalyst and in the presence of an aliphatic carboxylic acid ester as a diluent in a reaction zone, which comprises: effecting the reaction at temperatures of 62° to 90° C. over a period of less than 20 minutes with the use of the diluent and acetaldehyde in a quantitative ratio of 60:40 to 40:60; delivering the resulting reaction products to a distilling zone; distilling overhead the carboxylic acid ester and water; separating the carboxylic acid ester phase from the water phase and recycling the organic phase with a reflux ratio of at least 1:1 to the distilling zone; delivering base product accumulating in the distilling zone to an evaporating zone and evaporating it therein so as to obtain 2 to 12 parts by weight of an acetic acid/acetic anhydride-mixture as distillate per part by weight of catalyst solution as base product.

2. A process as claimed in claim 1, wherein the gaseous oxygen is admitted to the reaction zone through a plurality of openings arranged at different levels.

3. A process as claimed in claim 1 or 2, wherein the reaction zone is fed with a quantity of gaseous oxygen necessary to have an oxygen concentration of less than 5 volume % in the issuing gas.

* * * * *